US010335050B2

(12) United States Patent
Hallab

(10) Patent No.: US 10,335,050 B2
(45) Date of Patent: Jul. 2, 2019

(54) APPARATUS AND METHOD FOR DETERMINING THE SPEED OF PROPAGATION OF A PULSE WAVE

(71) Applicant: Magid Hallab, Saint Nicolas de Redon (FR)

(72) Inventor: Magid Hallab, Saint Nicolas de Redon (FR)

( * ) Notice: Subject to any disclaimer, the term of this patent is extended or adjusted under 35 U.S.C. 154(b) by 598 days.

(21) Appl. No.: 14/889,660

(22) PCT Filed: Apr. 29, 2014

(86) PCT No.: PCT/FR2014/051026
§ 371 (c)(1),
(2) Date: Nov. 6, 2015

(87) PCT Pub. No.: WO2014/181056
PCT Pub. Date: Nov. 13, 2014

(65) Prior Publication Data
US 2016/0073911 A1    Mar. 17, 2016

(30) Foreign Application Priority Data

May 6, 2013   (FR) ..................................... 13 54131

(51) Int. Cl.
*A61B 5/0285* (2006.01)
*A61B 5/02* (2006.01)
(Continued)

(52) U.S. Cl.
CPC ........ *A61B 5/0285* (2013.01); *A61B 5/02007* (2013.01); *A61B 5/02028* (2013.01);
(Continued)

(58) Field of Classification Search
CPC . A61B 5/0285; A61B 5/7278; A61B 5/02028; A61B 5/0261; A61B 5/02433;
(Continued)

(56) References Cited

U.S. PATENT DOCUMENTS

2008/0027330 A1    1/2008   Naghavi et al.

FOREIGN PATENT DOCUMENTS

FR    2947167 A1    12/2010

OTHER PUBLICATIONS

International Search Report dated Sep. 24, 2014, for corresponding International Application No. PCT/FR2014/051026 filed Apr. 29, 2014.
English translation of the Written Opinion dated Sep. 24, 2014, for corresponding International Application No. PCT/FR2014/051026 filed Apr. 29, 2014.

(Continued)

*Primary Examiner* — Mark Bockelman
(74) *Attorney, Agent, or Firm* — David D. Brush; Westman, Champlin & Koehler, P.A.

(57) ABSTRACT

An apparatus and method are provided for determining the speed of propagation of a pulse wave. The apparatus includes at least one pulse wave sensor positionable on a finger and a toe of a subject and a processing and calculation unit configured to determine the time that the pulse wave reaches the finger and the time that the pulse wave reaches the toe of the subject. The unit calculates a time value, designated "aortic transit time", as a function of the difference between the times that the pulse wave reaches the toe or the finger of the subject, and calculates a speed, designated "aortic pulse wave velocity", as a function of the aortic transit time. The calculation includes division of a value, designated "aortic length", as a function of the height and age of the subject, by the aortic transit time.

19 Claims, 6 Drawing Sheets

(51) Int. Cl.
*A61B 5/026* (2006.01)
*A61B 5/00* (2006.01)
*A61B 5/024* (2006.01)
*A61B 5/021* (2006.01)

(52) U.S. Cl.
CPC ........ *A61B 5/0261* (2013.01); *A61B 5/02125* (2013.01); *A61B 5/02433* (2013.01); *A61B 5/6826* (2013.01); *A61B 5/6829* (2013.01); *A61B 5/7225* (2013.01); *A61B 5/7278* (2013.01); *A61B 5/02* (2013.01); *A61B 5/6838* (2013.01)

(58) Field of Classification Search
CPC . A61B 5/7225; A61B 5/6826; A61B 5/02125; A61B 5/02007; A61B 5/6829; A61B 5/6838
See application file for complete search history.

(56) References Cited

OTHER PUBLICATIONS

Juan M. Padilla et al., "Pulse Wave Velocity and Digital Volume Pulse as Indirect Estimators of Blood Pressure: Pilot Study on Healthy Volunteers", Cardiovascular Engineering: An International Journal, Kluwer Academic Publishers-Plenum Publishers, NE, vol. 9, No. 3, Aug. 6, 2009 (Aug. 6, 2009), pp. 104-112, XP019728147.
Nitzan M. et al., The difference in pulse transit time to the toe and finger measured by photoplethysmograpy; Difference in pulse transit time to the toe and finger:, Pysiological Measuremetn, Institute of Physics Publishing, Bristol, GB, vol. 23, No. 1, Dec. 19, 2001 (Dec. 19, 2001), pp. 85-93, XP020073583.
Magid Hallab et al., "Relationship between the aortic valves and an anatomical landmark using chest CT scan", Artery Research, vol. 6, No. 1, Mar. 1, 2012 (Mar. 1, 2012), pp. 55-57, XP055141870.
M. Hallab et al., "Un Nouvel Index Pour Evaluer de Vieillissement arterielle: Popscore", Annales de Cardiologie et D'Angeioligie, vol. 61, No. 3, May 8, 2012, pp. 184-187, XP055099934, and English Machine Translation.

APPARATUS AND METHOD FOR DETERMINING THE SPEED OF PROPAGATION OF A PULSE WAVE

CROSS-REFERENCE TO RELATED APPLICATIONS

This Application is a Section 371 National Stage Application of International Application No. PCT/FR2014/051026, filed Apr. 29, 2014, the content of which is incorporated herein by reference in its entirety, and published as WO 2014/181056 on Nov. 13, 2014, not in English.

FIELD OF THE DISCLOSURE

The present invention concerns in a general manner the determining of the speed of propagation of a blood pressure wave, known as a pulse wave, of a subject.

BACKGROUND OF THE DISCLOSURE

The speed of propagation of the pulse wave is a parameter which permits an assessment of the physical state of the arteries through which said wave is propagated, with a view to estimating the cardiovascular risk in a subject. The risk of cardiovascular accident can result in particular in the following risks for the organs of the subject:
the heart: angina pectoris, infarction
the brain: cerebral haemorrhage or ischaemia;
the kidney: renal failure;
the aorta: aneurysm, dissection.

Methods are known from the prior art for determining the speed of propagation of the pulse wave, which are used to determine a pulse wave index, as a function of the pulse wave velocity measured between the heart and a finger, and of the pulse wave velocity measured between the heart and a toe. Such a method is described in the patent application published under number FR2947167 and allows a possible cardiovascular risk to be determined.

To further improve the determining of risks linked to arterial stiffness, it is desirable to be able to use another method and another corresponding apparatus, i.e. an alternative method and apparatus to the solution known from the prior art, whilst maintaining a reliability and a repeatability of the measurements.

SUMMARY

An aspect of the present disclosure relates to an apparatus for determining the speed of propagation of a blood pressure wave of a subject, known as a pulse wave, said apparatus including either one pulse wave sensor or a first and a second pulse wave sensor, said or each sensor being able to be positioned at a finger or at a toe of the subject, said apparatus also including a processing and calculation unit configured for:
determining the time that a pulse wave reaches a finger of the subject, when said sensor or one of said sensor(s) is positioned on said finger;
determining the time that a pulse wave reaches a toe of the subject, when said sensor or one of said sensor(s) is positioned on said toe;
calculating a time value, designated aortic transit time, as a function of the difference between said times that a pulse wave reaches a finger or a toe;
calculating said pulse wave propagation speed, designated aortic pulse wave velocity, as a function of said aortic transit time, said calculation including the division of a value, designated aortic length (Laort), a function of the height (H) and of the age of the subject, by said aortic transit time (Top_aort),
said apparatus further including, when it includes a single pulse wave sensor, means (2) for measurement of the cardiac activity of the subject, intended to permit a detection of the time of start (TA) of the pulse wave.

In other words, the aortic pulse wave velocity is obtained by a calculation taking into account the difference of arrival time of the pulse wave between a toe and a finger and an estimation of the aortic length depending on the height and age of the subject.

The applicant has in fact been able to note through tests that the aortic length is substantially proportional to the height of the subject and varies as a function of the age of the subject.

As detailed herein below, the fact of calculating a time value as a function of the difference between the time that a pulse wave reaches the toe and the time that a pulse wave reaches the finger permits a transit time to be obtained, which corresponds to the transit time of a pulse wave in the aorta.

The calculation of the transit time of the pulse wave in the aorta thus permits a determining of the speed of propagation of the pulse wave in the aorta, which is a physical parameter representative in a reliable and repeatable manner of the arterial stiffness of the subject.

In fact, the aorta principally includes elastic tissues. Thus, a possible increase of the arterial stiffness of the subject results at the level of the aorta of the subject in a reduction of the elastic properties of the tissues of the aorta and therefore an increase of the pulse wave velocity at the level of the aorta.

The impact of a possible increase of the arterial stiffness is thus more significant on the aorta than on the circulation circuit from the heart to the finger and from the start of the femoral artery to the toe, such that the determining of the pulse wave velocity at the level of the aorta permits one to have at one's disposal a parameter representative in a reliable and repeatable manner of the arterial stiffness.

Furthermore, the fact of positioning the or each sensor at the end of a limb to detect the arrival of the pulse wave permits a determining of this time of arrival of the wave in a reliable and reproducible manner.

To summarize, the apparatus according to the invention permits a calculating of a speed, corresponding to that of the aortic pulse wave, as function of the difference in transit time of a pulse wave between a toe and a finger and of the aortic length, which then permits the identifying in a reliable and repeatable manner of a possible increase in the arterial stiffness and subsequently the evaluating of a potential risk level linked to this stiffness, such as a cardiovascular risk.

According to an advantageous characteristic, the calculation of the aortic length includes the multiplication of the height of the subject by a coefficient dependent on the age of the subject comprised in the range [0.3; 0.4].

In a particularly advantageous embodiment of the invention, said coefficient varies as a function of the age such that said aortic length increases by 0.9 to 1.1 cm per additional decade, preferably by 1.0 cm per additional decade.

In a particular embodiment of the invention, said coefficient is equal to $(0.336+0.0006*AGE)$ with the age AGE in years.

Preferably, said aortic pulse wave velocity (Vop_aort) is expressed in the form of an affine function of the relationship of said aortic length (Laort) over said aortic transit time (Top_aort).

The applicant has in fact noted, in an unprecedented manner, that the aortic pulse wave velocity is not directly proportional to the relationship between the aortic length and the aortic transit time, but varies in an affine manner as a function of the preceding relationship.

According to an advantageous characteristic of the invention, the processing and calculation unit includes instructions for calculating the aortic pulse wave velocity in the following manner:

$$Vop\_aort = a_1 * Laort/Top\_aort - b_1;$$

with Vop_aort the aortic pulse wave velocity in meters per second, Top_aort the aortic transit time in seconds, Laort the aortic length in meters, $a_1$ a constant comprised between 1.25 and 1.65, preferably substantially equal to 1.4, and $b_1$ a constant comprised between 1 and 1.6, preferably substantially equal to 1.5.

According to an advantageous characteristic of the invention, said apparatus including means for measurement of the cardiac activity of the subject, such as an electrocardiograph permitting the detecting of the time of start of the pulse wave, said aortic transit time is equal to the difference between the time in between the time that the pulse wave reaches the toe and the time of start of the pulse wave, and the time in between the time that the pulse wave reaches the finger and the time of start of the pulse wave.

According to an advantageous characteristic of the invention, the means for measurement of cardiac activity of the subject are formed by an electrocardiograph able to generate an electrocardiogram presenting in particular a periodic amplitude variation of the electrical signal of cardiac activity, designated QRS complex, the processing and calculation unit being configured to determine the time of start of the pulse wave from the heart from the wave R of the said QRS complex, the processing and calculation unit being preferably configured to associate the time of start of the pulse wave from the heart to the corresponding time at the end of the wave R of the QRS complex.

According to a particular aspect, the two times of that a pulse wave reaches a finger or a toe are included in a range of time values of an extent comprised between 1 and 200 milliseconds.

The use of a given range of time to identify the pulse wave arrival times permits it to be ensured that said times of arrival used for calculating the aortic transit time are in fact the times of arrival at the different limbs of the same pulse wave, and thus allows said calculation of aortic transit time to be realized without having to know the time of start of the pulse wave.

Advantageously, said or each pulse wave sensor is formed by a light emitter and light receiver, preferably operating in infrared.

Preferably, the pulse wave sensor is carried by a clip, permitting the fixing of said sensor on the end of the limb. The fact of using a clip for the positioning of the sensor at the end of a limb of the subject permits the stabilizing of the signal of the detected pulse wave at the level of this limb.

The apparatus according to the invention can be designed in the form of a portable apparatus of small overall dimensions and easy to handle, permitting a non-invasive measuring of the pulse wave velocity, and requiring a minimum of intervention on the part of the operator.

Preferably, the end of the limb selected is the end of the middle finger (longest finger) for the hand, and the end of the second toe for the foot (longest small toe), offering a better chance of picking up the light which passes through the pad of said finger or toe.

The invention also concerns a method for determining the speed of propagation of a blood pressure wave, known as a pulse wave, of a subject, characterized in that it comprises the following steps:

a)—determining of the time that a pulse wave reaches a finger of the subject, at which a sensor, known as a pulse wave sensor, is positioned, b)—determining of the time that a pulse wave reaches a toe of the subject, at which a sensor, known as a pulse wave sensor, is positioned, c)—calculating of a time value, designated aortic transit time, as a function of the difference between said times that a pulse wave reaches a finger or a toe;

d)—calculating of said pulse wave propagation speed, designated aortic pulse wave velocity, as a function of said aortic transit time, said calculating including the division of a value, designated aortic length, as a function of the height and of the age of the subject, by said aortic transit time.

According to a particular embodiment, the steps a) and b) are realized successively, in order or reverse direction, with a single and same pulse wave sensor. In this case, the sensor is firstly positioned at the finger or at the toe, then at the toe or at the finger. In this case, the time of start of each pulse wave is detected with the aid of means for measurement of the cardiac activity of the subject.

According to another particular embodiment, the steps a) and b) are realized with two distinct pulse wave sensors, one positioned at the finger and the other at the toe.

According to an advantageous characteristic of the method according to the invention, the aortic pulse wave velocity is calculated by means of the formula:

$$Vop\_aort = a_1 * Laort/Top\text{-}aort - b_1, \text{ as explained above.}$$

According to an advantageous characteristic of the method according to the invention, said method includes the determining of the time of start of the pulse wave with the aid of means for measurement of the cardiac activity of the subject, and said aortic transit time is equal to the difference between the time in between the time that the pulse wave reaches the toe and the time of start of the pulse wave, and the time in between the time that the pulse wave reaches the finger and the time of start of the pulse wave.

According to an advantageous characteristic of the method according to the invention, the two times that a pulse wave reaches a finger or a toe of the subject are included in a range of time values of an extent comprised between 1 and 200 milliseconds.

BRIEF DESCRIPTION OF THE DRAWINGS

The invention will be better understood on reading the following description of example embodiments, with reference to the attached drawings, in which.

DETAILED DESCRIPTION OF ILLUSTRATIVE EMBODIMENTS

With reference to the figures and as quoted above, the invention concerns an apparatus 1 for determining the speed of propagation of a blood pressure wave of a subject, known as a pulse wave. The pulse wave corresponds to the blood flow sent by the heart in various parts of the body on each beat of the heart.

Figure 1:
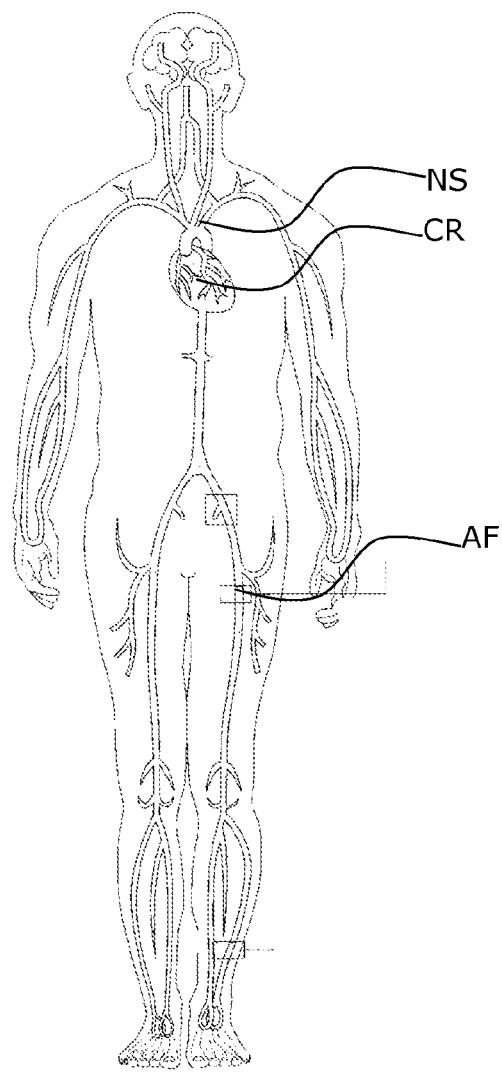
FIG. 1 is a diagrammatic view of the body of a subject, showing the locations of the sternal node, annotated NS, and the start of the femoral artery, annotated AF.
Figure 2:
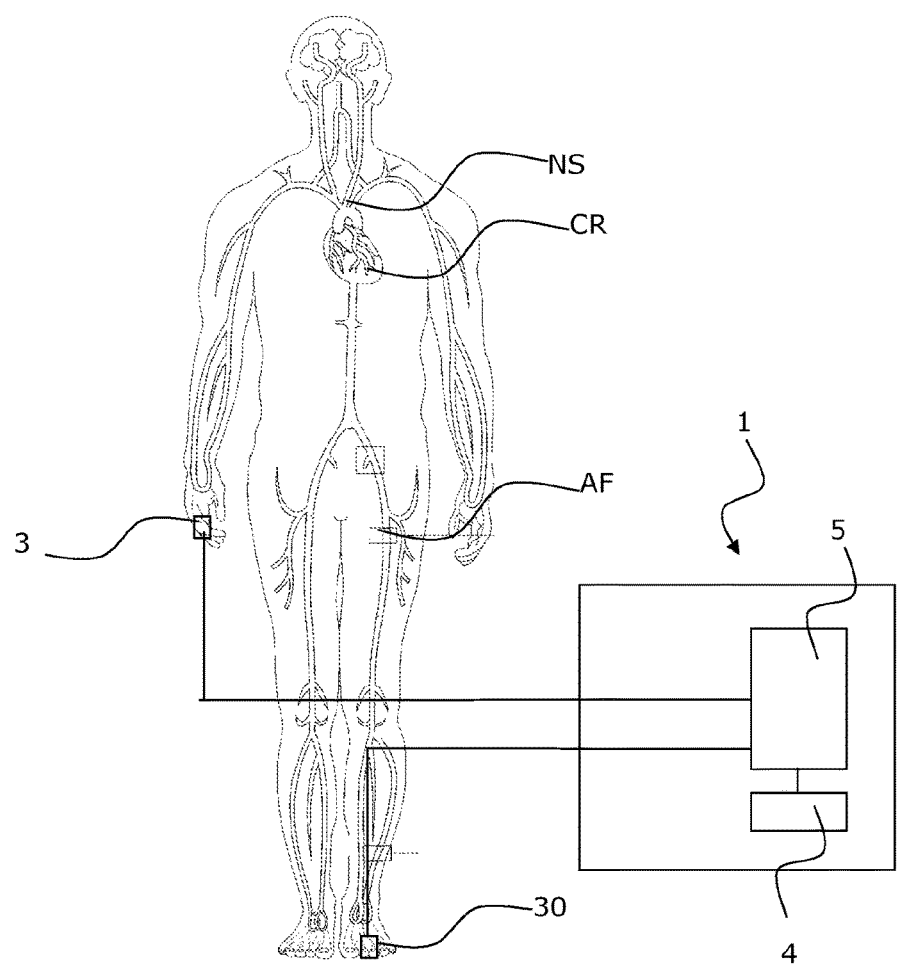
FIG. 2 is a diagrammatic view of an apparatus according to an embodiment of the invention in the positioned state of the pulse wave sensors at a finger and at a toe of the subject, said apparatus being without means for detection of cardiac activity.
Figure 3:
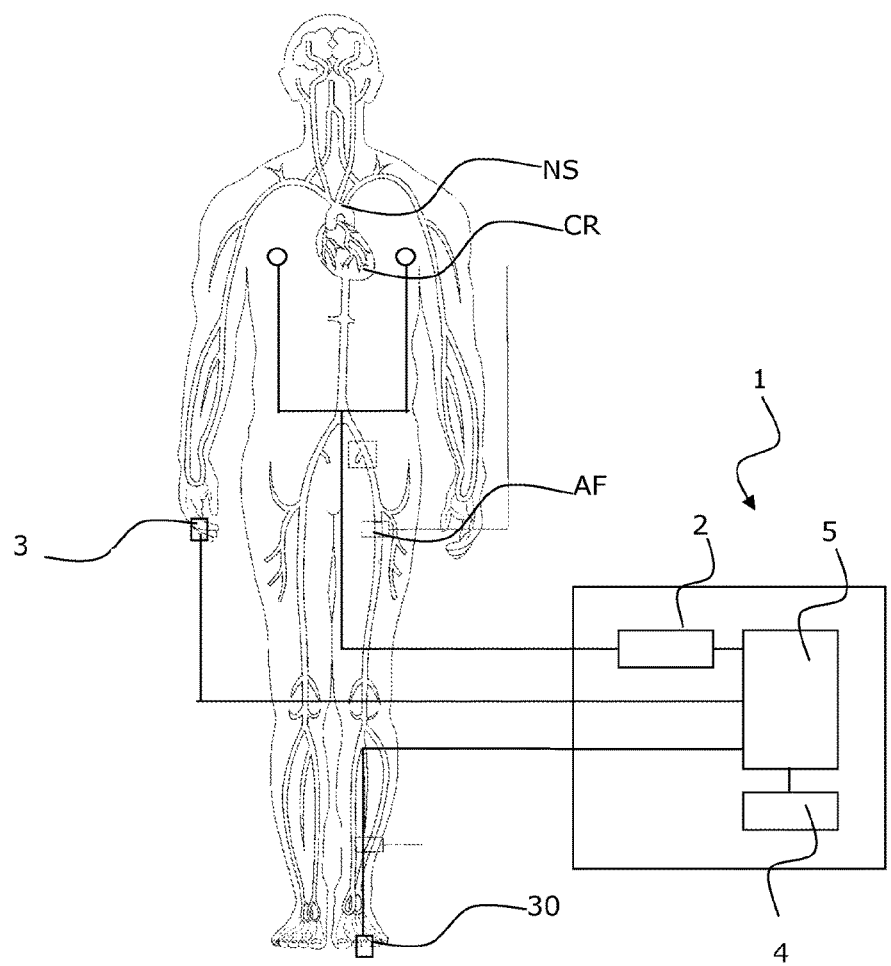
FIG. 3 is a diagrammatic view of an apparatus according to an embodiment of the invention in the positioned state of the sensors at a finger and at a toe of the subject, and in the positioned state of means for detection of cardiac activity on the body of the subject.

According to an embodiment of the invention illustrated in FIGS. 2 and 3, said apparatus includes a first and a second pulse wave sensor 3, 30. One, 3, of the sensors is intended to be positioned at a finger of a hand and the other sensor 30 at a toe of a foot of the subject. As detailed hereinbelow, the embodiment of FIG. 3 is distinguished from that of FIG. 2 by the fact that in the embodiment of FIG. 3, the apparatus is provided with a cardiac activity measurement device 2 for measurement of the cardiac activity of the subject, such as an electrocardiograph. According to a variant embodiment detailed hereinbelow and illustrated in FIG. 4, provision can be made that the apparatus includes a single pulse wave sensor.

The or each pulse wave sensor 3, 30 permits the detecting of the passage of the pulse wave corresponding to the wave of the blood flow sent by the heat in the different parts of the body of the subject and in particular to the end of the limb at which said sensor is positioned.

The or each pulse wave sensor 3, 30 permits the acquisition in time of the amplitude of a parameter of the blood flow and/or of the blood vessel in which said blood flow circulates at the site where the sensor is positioned, said parameter being representative of the pressure wave formed by said blood flow.

The measured parameter can be a pressure parameter measured via the pressure which the wall of the vessel undergoes due to the passage of the blood flow through said vessel. In this case, the pulse wave sensor is a pressure sensor configured to measure the variations in pressure undergone by the wall of the blood vessel on the surface of which the sensor is disposed.

The measured parameter can also be a parameter of reflection and/or transmission of a light by or through the blood vessel. In this case, the or each pulse wave sensor 3 is formed by a light emitter and a light receiver, preferably infrared.

In other words, the or each pulse wave sensor measures a parameter, the variations of which in time permit the determining of the time of passage of the pulse wave at the site where said pulse wave sensor is positioned.

Advantageously, said or each pulse wave sensor is carried by a clip to permit a stable positioning by clipping of said sensor at the end of the selected limb of the subject.

In a variant, said or each pulse wave sensor can be a Doppler effect, piezoelectric, or other sensor.

Said apparatus also includes a processing and calculation unit 5. The unit includes a memory in which data can be stored, in particular the height, annotated H, of the subject and the age of the subject. Said processing and calculation unit 5 is preferably formed by a microprocessor. When it is stated below in the description that the processing and calculation unit 5 is configured to realize a given operation, this signifies that the microprocessor includes data processing instructions permitting said operation to be carried out.

Said processing and calculation unit 5 is able to communicate with the or each sensor 3, 30 and the measurement device 2 for measurement of the cardiac activity when they are present. Provision can be made that the sensor(s) and/or the device for measurement of cardiac activity communicate in a wired manner or by radio (Hertzian) waves with the processing and calculation unit.

The apparatus also includes a data input interface 4 configured to permit the input of at least the height H and the age of the patient. In the example illustrated in the figures, said data input interface 4 is a man-machine interface 4 which includes for example a display screen and data input means, such as buttons, keyboard or entry window of a touch screen.

With reference to FIG. 2 or 3, said unit 5 includes instructions to determine, with the aid of the sensor 3 positioned at the finger, the time TB that a pulse wave reaches the said finger, and to determine, with the aid of the sensor 30 positioned at the toe, the time TC that this pulse wave reaches the toe.

Said unit 5 then calculates a time value, designated aortic transit time, annotated Top_aort, corresponding to the difference between said times that the pulse wave reaches the toe and the finger: TC−TB. Provision can be made to take the absolute value of this difference.

The unit 5 then calculates a speed annotated Vop_aort, designated aortic pulse wave velocity, dependent on the relationship between the aortic length Laort, as a function of the height, annotated H, and of the age of the subject, and said aortic transit time Top_aort.

Advantageously, the calculation of the aortic length Laort includes the multiplication of the height (H) of the subject by a coefficient dependent on the age of the subject comprised in the range of values [0.3; 0.4].

More precisely, the processing and calculation unit 5 includes instructions for calculating the aortic pulse wave velocity in the following manner:

$$Vop\_aort = a_1 * Laort/Top\_aort - b_1$$

with Vop_aort the aortic pulse wave velocity in meters per second, Top_aort the aortic transit time in seconds, Laort the aortic length in meters, $a_1$ a constant equal to 1.43 and $b_1$ a constant equal to 1.53.

In this particular embodiment of the invention, the aortic length is calculated with the aid of the following formula: Laort (m)=H*(0.336+0.0006*AGE), where AGE is expressed in years.

In a variant, the pulse wave velocity can be calculated by the following formula:

$$Vop\_aort = ((H*K1/Top\_aort) - a)/b + c$$

with Voop_aort: the aortic pulse wave velocity in meters per second (m/s)

Top_aort: aortic transit time in seconds (s)

H: the height of the subject in meters (m)

K1 a coefficient dependent on the age of the subject comprised between 0.3 and 0.4, and a, b and c three constants comprised respectively between 2 and 4 m/s, between 0.6 and 0.8, and between 2 and 3 m/s, preferably substantially equal to 3, 0.7 and 2.76 respectively.

The length of the circuit of circulation of blood travelled by the pulse wave from the heart CR, at the level of the valves or aortic sigmoids, to the toe, is formed principally by the distance from the heart CR to the sternal node NS, the length from the sternal node NS to the start of the femoral artery AF (corresponding to the length of the aorta AORT), and the length from the start of the femoral artery AF to the toe.

Furthermore, the length of the circuit of circulation of blood travelled by the pulse wave from the heart CR to the finger is formed principally by the distance from the heart CR to the sternal node NS and the length from the sternal node NS to the finger.

Now, it is noted that the length from the start of the femoral artery AF to the toe corresponds substantially to the length from the sternal node NS to the finger.

Furthermore, the circulation circuit of blood from the heart CR to the finger and the circuit of circulation of blood from the start of the femoral artery AF to the toe are principally formed by muscular tissues. Thus, the pulse wave propagation speed is substantially the same along these two circuits.

As a result, the fact of calculating a time value corresponding to the difference between the time TC that the pulse wave reaches the toe and the time TB that the pulse wave reaches the finger permits a transit time to be obtained which corresponds to the transit time of the pulse wave in the aorta AORT.

The calculation of the pulse wave transit time in the aorta thus permits a determining of a pulse wave velocity in the aorta which, as explained above, is a physical parameter which is representative in a reliable and repeatable manner of the arterial stiffness of the subject.

As quoted above, according to the particular embodiment of the invention illustrated in FIG. 2, the apparatus does not include a device for measurement of the cardiac activity of the subject permitting the detection of the time of start of the pulse wave, so that unit 5 verifies that the two times of arrival TB, TC of pulse wave are included in a window or range of time values of an extent comprised between 1 and 200 milliseconds, so as to ensure that the two times of arrival TB, TC indeed correspond to the same pulse wave.

According to the particular embodiment of the invention illustrated in FIG. 3, said apparatus includes a device 2 for measurement of the cardiac activity of the subject, such as an electrocardiograph. The device 2 for measurement of the cardiac activity of the subject are formed by an electrocardiograph able to generate an electrocardiogram presenting in particular a periodic amplitude variation of the electrical signal of cardiac activity, designated QRS complex. The processing and calculation unit 5 is configured to determine the time of start of the pulse wave from the heart from the R wave of the said QRS complex. For further details, the person skilled in the art will consult the patent application published under number FR2947167, which describes examples of determination method of the time of start of the pulse wave from the heart from the R wave of the said QRS complex.

Thus, according to the embodiment illustrated in FIG. 3, the said unit 5 is configured to detect the time of start TA of the pulse wave with the aid of the said device 2 for measurement of the cardiac activity of the subject. The said aortic transit time Top_aort is equal to the difference between the time, annotated DELTATC, in between the time that the pulse wave reaches the toe TC and the time of start TA of the pulse wave, and the time, annotated DELTATB, in between the time that the pulse wave TB reaches the finger and the time of start TA of the pulse wave.

In the example illustrated in FIGS. 2 and 3, the apparatus includes two pulse wave sensors 3, 30, which permits a determining of the times that a same pulse wave reaches the finger and the toe, and hence the aortic transit time with or without knowledge of the time of start of the said pulse wave. Thus, the pulse waves measured in an upper limb (hand) and in a lower limb (foot) originate from the same blood wave emitted by the heart, which improves the reliability of the calculation.

Figure 4:
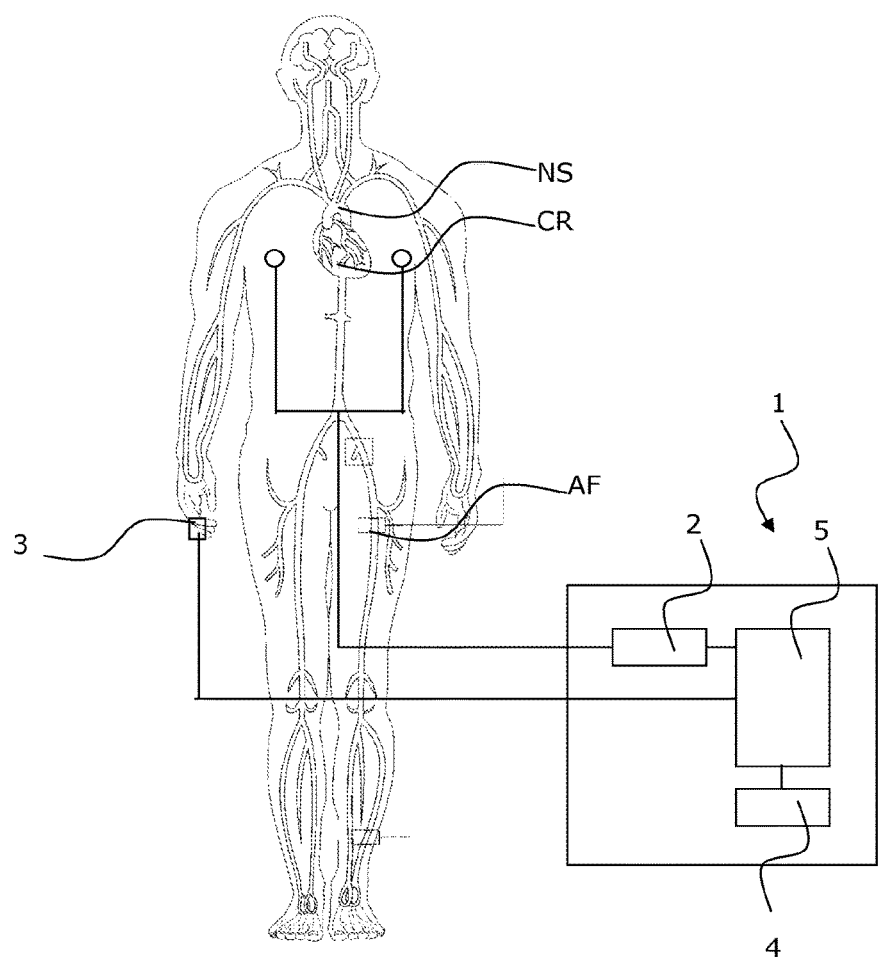
FIG. 4 is a diagrammatic view of an apparatus according to another embodiment of the invention, for which said apparatus includes means for detection of cardiac activity and a single pulse wave sensor.
Figure 5:
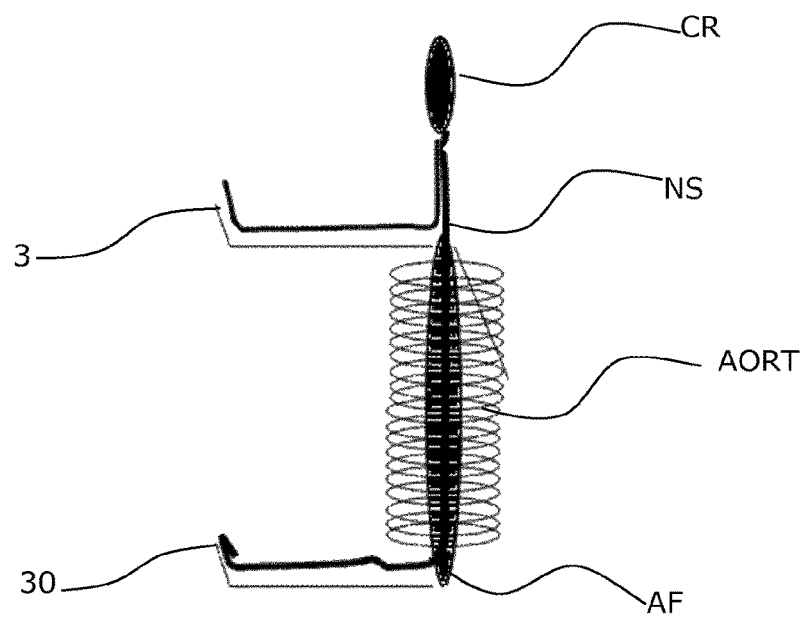
FIG. 5 is a diagrammatic view of the circulation circuit of the blood from the heart, annotated CR, to a finger, and from the heart to a toe.

In a variant, as illustrated in FIG. 4, provision can be made that the apparatus is equipped with a single pulse wave sensor 3 which can be intended to be positioned at the finger to measure the time of arrival that a pulse wave reaches the finger, then at the toe to measure the time that another pulse wave reaches the toe, or vice versa.

The apparatus permits the implementation of a method for determining the propagation speed of the aortic pulse wave of a subject in the following manner. The or each pulse wave sensor is held by a clip at the end of a toe or finger. The height H and age of the subject are entered into the apparatus via the corresponding input interface 4.

Figure 6:
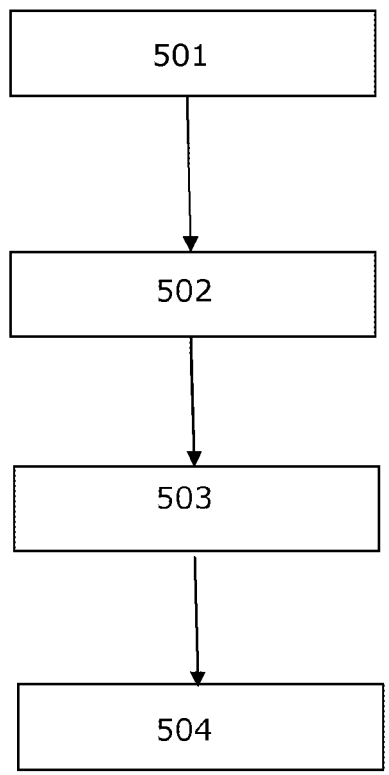
FIG. 6 is a block diagram illustrating the steps of the method according to an embodiment of the invention.

As illustrated in FIG. 6, at the step 501, the unit 5 determines the time of arrival TB of a pulse wave at a finger of a hand of the subject at the level of which there is positioned a pulse wave sensor, and, at the step 502, the time of arrival TC of a pulse wave at a toe of the subject at the level of which there is positioned a pulse wave sensor. The time of arrival of a pulse wave can be determined from different characteristic points of the wave, such as: foot of the wave, inflection point of the ascending phase of the wave, the peak of the wave, or the point of intersection of the tangent of the ascending curve of the wave with the base line, or else the centre of gravity of the wave (i.e. the centre of gravity of the surface defined by the form of the curve of the wave).

As explained above, the sensor positioned at the finger and the sensor positioned at the toe can be formed by a single sensor moved from the finger to the toe or vice versa. When the apparatus uses two distinct sensors, the time of arrival TB and the time of arrival TC can be the times of arrival of the same pulse wave, whereas in the case of a sensor positioned successively at the end of one limb then of another, the measurements are staggered in time such that the pulse wave associated with the determined time of arrival TB is a pulse wave generated at a different time to that associated with the determined time of arrival TC.

In the case where the times TB and TC are associated with the same pulse wave, it is possible to calculate (step 503) the aortic transit time Top_aort, by simply forming the difference between the said times of arrival TB, TC, since the time of start is the same. Preferably, the unit 5 verifies that the two times of arrival TB, TC are included in a window or range of time values of an extent comprised between 1 and 200 milliseconds.

Conversely, when the times TB and TC are associated with two pulse waves generated at different times, a calculation should be made (step 503) of the aortic transit time Top_aort, taking into account the times of start of each pulse wave, as explained above.

Then, at step 504, the speed Vop_aort, designated aortic pulse wave velocity, is calculated from the division of a value, designated aortic length Laort, as a function of the height (H) of the subject, by said aortic transit time Top_aort.

Preferably, the formula:

$$Vop\_aort = a_1 * Laort/Top\_aort - b_1$$

is applied, as detailed above.

In the case where an apparatus is used, provided with an electrocardiograph, for determining the time of start of each pulse wave at the finger and at the toe, said electrocardiograph can be used in the following manner. The two electrodes of the electrocardiograph are applied on two distinct areas of the body of the subject. To do this, it is possible to make provision that the subject places his/her two thumbs on the two corresponding electrodes of the electrocardiograph of the apparatus.

During the acquisition by unit 5 of the apparatus of the pulse wave signals, and possibly of the signals of cardiac activity, provision can be made that these signals are preconditioned, then subjected to an analog filtering and to an amplification. Unit 5 can then proceed to a digitization and digital filtering operation to obtain at the output data transmitted to a calculation program which is internal to the apparatus or is executed on an external device, such as a desktop computer, laptop, tablet or smartphone. Once the height and the age of the subject are entered into this program, the latter can calculate, possibly linked by internet with a data analysis and calculation centre, the aortic pulse wave velocity as explained above. The result of the calculation can be displayed on the apparatus or on an external device.

An exemplary embodiment of the present invention proposes an alternative apparatus and method to the solution known from the prior art, which permits the determining in a reliable and repeatable manner of a physical parameter of a subject, the value of which varies in a reliable manner with the arterial stiffness of the said subject.

An exemplary embodiment proposes an apparatus and a method for determining the speed of propagation of a pulse wave which are easy and quick to use or to put into operation, even for a person who does not possess medical expertise.

The present invention is in no way limited to the embodiments which are described and represented, but the person skilled in the art will bring to it any variant in accordance with its essence.

The invention claimed is:

1. An apparatus for determining speed of propagation of blood pressure waves of a subject, known as pulse waves, said apparatus comprising:
   at least one wave pulse sensor, each wave pulse sensor being able to be positioned on a finger of a hand or on a toe of a foot of the subject;
   a processor; and
   at least one non-transitory computer-readable medium comprising values stored thereon representing a height (H) and an age of the subject and comprising instructions stored thereon, which when executed by the processor configure the apparatus to perform acts comprising:
      using a first of the at least one sensor to determine a time (TB) that a pulse wave reaches the finger of the subject, when said first sensor is positioned on said finger;
      using the first or a second of the at least one sensor to determine a time that a pulse wave reaches a toe of the subject, when said first or second sensor is positioned on said toe;
      calculating a time value, designated aortic transit time (Top_aort), as a function of the difference between said times that a pulse wave reaches the toe and the finger of the subject (TC, TB);
      calculating said pulse wave propagation speed, designated aortic pulse wave velocity (Vop_aort), as a function of said aortic transit time (Top_aort), said calculation including dividing a value, designated aortic length (Laort), as a function of the stored values representing the height (H) and age of the subject, by said aortic transit time (Top_aort).

2. The apparatus according to claim 1, wherein said aortic length (Laort) is obtained by multiplying the height (H) of the subject by a coefficient as a function of the age of the subject, comprised in the range [0.3; 0.4].

3. The apparatus according to claim 2, wherein said coefficient varies as a function of the age, such that said aortic length increases by 0.9 to 1.1 cm per additional decade.

4. The apparatus according to claim 1, wherein said aortic pulse wave velocity (Vop_aort) is expressed in the form of an affine function of the relationship of said aortic length (Laort) over said aortic transit time (Top_aort).

5. The apparatus according to claim 4, wherein said aortic pulse wave velocity is expressed in the following manner:
   $Vop\_aort = a_1 * Laort/Top\_aort - b_1$;
   with Vop_aort the aortic pulse wave velocity in meters per second, Top_aort the aortic transit time in seconds, Laort the aortic length in meters, $a_1$ a constant substantially equal to 1.4, and $b_1$ a constant substantially equal to 1.5.

6. The apparatus according to claim 1, wherein said apparatus including a single pulse wave sensor, said aortic transit time (Top_aort) is equal to the difference between the time (DELTATC) in between the time that a first pulse wave reaches the toe (TC) and a time start of the first pulse wave's start (TA), and the time (DELTATB) in between the time that a second pulse wave reaches the finger (TB) and the time of start of the second pulse wave.

7. The apparatus according to claim 1, wherein the at least one pulse wave sensor is formed by a light emitter and a light receiver.

8. The apparatus of claim 1, wherein said apparatus comprises a single wave pulse sensor, referred to as the first pulse wave sensor, and further comprises a cardiac activity measuring device configured to measure cardiac activity of the subject and detect a time of start of the pulse wave.

9. A method for determining speed of propagation of blood pressure waves, known as pulse waves, of a subject, wherein the method comprises the following acts:
   a) using a first pulse wave sensor, determining a time that a pulse wave reaches (TB) a finger of the subject, at which the first pulse wave sensor is positioned,
   b) using the first pulse wave sensor or a second pulse wave sensor, determining a time that a pulse wave reaches (TC) a toe of the subject, at which the first or the second pulse wave sensor is positioned,
   c) calculating a time value, designated aortic transit time (Top_aort), as a function of the difference between said times that a pulse wave reaches the finger and the toe of the subject (TB, TC);
   d) calculating said pulse wave propagation speed, designated aortic pulse wave velocity (Vop_aort), as a function of said aortic transit time (Top_aort), including division of a value, designated aortic length (Laort), as a function of a height and an age of the subject, by said aortic transit time (Top_aort).

10. The method according to claim 9, wherein the acts a) and b) are realized successively, in order or reverse order, with one and the same first pulse wave sensor.

11. The method according to claim 9, wherein the acts a) and b) are realized with two distinct pulse wave sensors, the first positioned on the finger and the second positioned on the toe.

12. The method according to claim 9, wherein the aortic pulse wave velocity is calculated according to the formula:

Vop_aort=$a_1$·Laort/Top_aort−$b_1$;

with Vop_aort being the aortic pulse wave velocity in meters per second, Top_aort being the aortic transit time in seconds, Laort being the aortic length in meters, $a_1$ being a constant substantially equal to 1.4 and $b_1$ being a constant substantially equal to 1.5.

13. The method according to claim 9, wherein said method includes determining a time of start (TA) of the pulse wave using a cardiac activity measurement device for measuring cardiac activity of the subject, and said aortic transit time (Top_aort) is equal to the difference between the time (DELTATC) in between the time that a first pulse wave reaches (TC) the toe and the time of start (TA) of the first pulse wave, and the time (DELTATB) in between the time that a second pulse wave reaches (TB) the finger and the time of start (TA) of the second pulse wave.

14. The method according to claim 9, wherein the times that a pulse wave reaches the finger or the toe of the subject (TB, TC) are included in a range of time values of an extent comprised between 1 and 200 milliseconds.

15. The method according to claim 9, wherein said aortic length (Laort) is obtained by multiplying the height (H) of the subject by a coefficient as a function of the age of the subject, comprised in the range [0.3; 0.4].

16. The method according to claim 15, wherein said coefficient varies as a function of the age, such that said aortic length increases by 0.9 to 1.1 cm per additional decade.

17. The method according to claim 9, wherein said aortic pulse wave velocity (Vop_aort) is expressed in the form of an affine function of the relationship of said aortic length (Laort) over said aortic transit time (Top_aort).

18. The method according to claim 9, the first pulse wave sensor is formed by a light emitter and a light receiver.

19. The method of claim 9, wherein the acts of determining a time that a pulse wave reaches the finger, determining a time that a pulse wave reaches the toe, calculating the aortic transit time and calculating the aortic pulse wave velocity are performed by a processor, which is coupled to the first pulse wave sensor or to the first and second pulse wave sensors, and which is configured by instructions stored on a non-transitory computer readable medium.

* * * * *